(12) United States Patent
Boehm et al.

(10) Patent No.: US 12,059,319 B2
(45) Date of Patent: Aug. 13, 2024

(54) SYRINGE ASSEMBLY

(71) Applicant: Solventum Intellectual Properties Company, Maplewood, MN (US)

(72) Inventors: Andreas J. Boehm, Reichling (DE); Marc Peuker, Schondorf (DE); Paul J. Homnick, Lake Elmo, MN (US); Bruce R. Broyles, Oakdale, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 193 days.

(21) Appl. No.: 17/597,599

(22) PCT Filed: Jul. 28, 2020

(86) PCT No.: PCT/IB2020/057118
§ 371 (c)(1),
(2) Date: Jan. 13, 2022

(87) PCT Pub. No.: WO2021/024093
PCT Pub. Date: Feb. 11, 2021

(65) Prior Publication Data
US 2022/0346910 A1    Nov. 3, 2022

(30) Foreign Application Priority Data
Aug. 2, 2019   (EP) .................................. 19189704

(51) Int. Cl.
*A61C 5/62*     (2017.01)
*A61C 5/50*     (2017.01)
(Continued)

(52) U.S. Cl.
CPC .................. *A61C 5/50* (2017.02); *A61C 5/62* (2017.02); *A61C 5/64* (2017.02); *A61M 3/005* (2013.01);
(Continued)

(58) Field of Classification Search
CPC ... A61C 5/50; A61C 5/62; A61C 5/64; A61M 3/0201; A61M 3/005; A61M 3/0262
(Continued)

(56) References Cited

U.S. PATENT DOCUMENTS 2,731,964 A * 1/1956 Emrich ................. A61M 5/001
604/199
3,767,085 A * 10/1973 Cannon ............. B05C 17/00566
604/82

(Continued)

FOREIGN PATENT DOCUMENTS

| EP | 2736447 | 6/2014 |
| EP | 2932936 | 10/2015 |

(Continued)

OTHER PUBLICATIONS

Product Information, "COMSUN Collapsible Dog Bowl, Foldable Expandable Cup Dish for Pet Cat Food Water Feeding Portable Travel Bowl Free Carabiner", A product of Amazon, Dec. 2015, (Online) URL: <https://www.amazon.com/COMSUN-Collapsible-Bowl-Expandable-Carabiner/dp/B019B53YVQ/ref=zg_bs_3024201011_1?_encoding=UTF8&psc=1&refRID=SZHK9MKS1403FCRRRQ0Y>, 8 pages.
(Continued)

*Primary Examiner* — Jeremy Carroll

(57) ABSTRACT

A syringe assembly being assembled from a syringe for dispensing a dental or medical substance, and a protective cover. The protective cover has a geometrically determined, non-foldable tubular protective shaft. The syringe has a cartridge having an outlet for the substance. Further, the cartridge and the protective cover are assembled with the cartridge being received within the protective shaft. The syringe further comprises a dispensing tip that is connected to the outlet for dispensing the substance from the dispensing tip. A first seal is provided between the dispensing tip
(Continued)

and the outlet, and a second seal is provided between the dispensing tip and the protective shaft.

12 Claims, 5 Drawing Sheets

(51) Int. Cl.
    *A61C 5/64*      (2017.01)
    *A61M 3/00*      (2006.01)
    *A61M 3/02*      (2006.01)

(52) U.S. Cl.
    CPC ......... *A61M 3/0201* (2021.05); *A61M 3/0262* (2013.01)

(58) Field of Classification Search
    USPC ................................... 222/129, 145.5, 145.6
    See application file for complete search history.

(56) References Cited

U.S. PATENT DOCUMENTS

| | | | |
|---|---|---|---|
| 5,188,617 A | 3/1993 | Linder | |
| 6,902,543 B1 | 6/2005 | Cherif-Cheikh | |
| 7,448,867 B2 | 11/2008 | Aloise | |
| 8,590,747 B2* | 11/2013 | Keller | A61B 17/8822 |
| | | | 222/137 |
| 9,283,059 B2* | 3/2016 | Pierson | A61C 9/0026 |
| 2002/0003462 A1 | 1/2002 | Stolk | |
| 2002/0068257 A1* | 6/2002 | Albach | A61C 9/0026 |
| | | | 433/90 |
| 2005/0075602 A1 | 4/2005 | Cherif-Cheikh | |
| 2021/0052818 A1* | 2/2021 | Ashraf | A61M 5/2033 |

FOREIGN PATENT DOCUMENTS

| | | |
|---|---|---|
| KR | 10-0848722 | 7/2008 |
| WO | WO 1993-011730 | 6/1993 |
| WO | WO 2002-040082 | 5/2002 |
| WO | WO 2020-115600 | 6/2020 |
| WO | WO 2021-165785 | 8/2021 |

OTHER PUBLICATIONS

Product Information, "Fasmov Silicone Collapsible Storage Bowls with Lids-Set of 3", A Product of Amazon, Nov. 2015, URL: <https://www.amazon.com/Fasmov-Silicone-Collapsible-Storage-Lids-Set/dp/B0185F07DG/ref=sr_1_6?hvadid=174235233280&hvdev=c&hvlocphy=21147&hvnetw=g&hvpos=1t1&hvqmt=e&hvrand=77993282627103989078&hvtargid=kwd-2601164742&keywords=collapsible+bowls&qid=1554841218&s=gateway&sr=8-6>, 11 pages.
Extended European Search Report for EP Application No. 19189704.0, mailed on Dec. 4, 2019, 2 pages.
International Search Report for PCT International Application No. PCT/IB2020/057118 mailed on Sep. 18, 2020, 5 pages.

* cited by examiner

SYRINGE ASSEMBLY

CROSS REFERENCE TO RELATED APPLICATIONS

This application is a national stage filing under 35 U.S.C. 371 of PCT/IB2020/057188, filed Jul. 28, 2020, which claims the benefit of European Application No. 19189704.0, filed Aug. 2, 2019, the disclosure of which is incorporated by reference in its/their entirety herein.

FIELD OF THE INVENTION

The invention relates to a syringe assembly, and in particular to a syringe assembly that comprises a syringe and a protective cover.

BACKGROUND ART

In dentistry dental substances are often provided from pre-filled syringes. In some cases it is desirable to apply the dental substances directly into a patient's mouth. In case of using a syringe a patient's mouth (i.e. intra-orally) such a syringe may get into contact with bacteria and other undesired material and therefore can be used with one patient only and typically only a single time. In case the same syringe is to be used for different patients and/or multiple times the syringe has to undergo a high level disinfection process or needs to be autoclaved.

Typically, existing methods of high level disinfecting, including for example autoclaving, cannot be used with many existing syringes, in particular in case they are pre-filled with a dental or medical substance. This because such high level disinfection methods often are based on high temperatures (for example 121° C. or 135° C.) which would affect the dental or medical substance. To avoid the need of high level disinfecting there are already hygiene covers in the form of disposable plastic sheath covers made out of a thin plastic film.

For example US 2002/3462 A1 discloses a thin flexible sleeve that receives a syringe without the syringe dispensing tip. After the syringe is received within the sleeve, the dispensing tip is affixed to the syringe which causes an end of the sleeve to open and to be physically impinged between the tip and the syringe. The syringe is thus protected from the operative environment.

Although existing covers provide certain advantages there is still a need for a cover that can be reused and which thus helps minimizing waste. Further, there is still a need for a cover that provides for maximized ergonomics of a syringe used with such a cover.

SUMMARY OF THE INVENTION

The invention relates to a syringe assembly. The syringe assembly comprises a syringe for dispensing a dental or medical substance. The syringe assembly further comprises a protective cover. The protective cover is preferably configured for encasing at least those portions of the syringe which are provided for operation, in particular manual operation of the syringe by a user. The protective cover is preferably further configured such that it can be removably combined with (or attached to) the syringe. Therefore, the protective cover may be removed from the syringe after use and can be disinfected separately in absence of the syringe. The so disinfected protective cover may be reused with the same or another syringe after.

The protective cover comprises a tubular protective shaft. The protective shaft preferably has a geometrically determined shape. The protective cover is preferably tailor-made based on the shape of the syringe. This means that preferably the protective cover fits precisely on the syringe at minimized play between the syringe and the protective cover. The protective shaft is further preferably non-foldable. Thus the protective shaft differs from a sleeve made from a plastic film. For example the protective cover, in particular the protective shaft, preferably does not have a welded or sealed joint. Such a welded or sealed joint, as typically present in plastic film-type protective sleeve may comprise sharp edges and sharp points that can feel uncomfortable when used in a patient's mouth and upon touching tissue. Further, any sound, for example as it may occur during wrinkling of a plastic film-type sleeve can be avoided.

The syringe has a cartridge that comprises an outlet for the substance. Further, the syringe comprises a dispensing tip that is connected to the outlet for dispensing the substance from the dispensing tip. The dispensing tip is preferably removably attachable to the cartridge.

The cartridge and the protective cover are assembled, with the cartridge being received within the protective shaft. The cartridge and the protective shaft are preferably assembled by inserting of the cartridge into the protective shaft. In other words the cartridge and the protective shaft are preferably assembled via telescopic mating or telescopic movement of the cartridge and the protective shaft relative to each other.

A first seal of the syringe assembly is provided between the dispensing tip and the outlet, and a second seal is provided between the dispensing tip and the protective shaft. The first seal is preferably provided for preventing any substance from leaking or escaping at the transition between the dispensing tip and the cartridge, whereas the second seal is preferably provided for preventing undesired material from penetrating through the transition between the dispensing tip and the protective shaft.

The invention is advantageous in that it helps maximizing the hygiene level in the use of syringes for dispensing dental or medical substances. The invention is further advantageous in that provides a protective cover that can be re-used, in particular a protective cover that can be disinfected using a high level disinfection method. Thus the invention helps minimizing waste, in particular helps minimizing plastic waste as it may occur using disposable covers.

The protective cover is configured such that the syringe can be operated for dispensing the substance from the syringe by only touching the protective cover and without touching the syringe. The syringe is configured so that it can be operated with or without the protective cover, although the advantages of the invention are provided in combination of the syringe and the protective cover only.

In a further embodiment the cartridge forms a chamber for the substance. The cartridge may form a single chamber for storing the substance in the form of a single component. Alternatively, the cartridge may form a first and a second chamber for storing the substance in the form of a first and a second component, respectively.

In an embodiment the syringe assembly further comprises a piston received at least partially within the chamber for expelling the substance from the chamber. The substance is preferably captured within the chamber between the piston and the outlet. In a syringe for storing the substance in the form of a first and second component, the first component is preferably captured within the first chamber between a first piston and a first outlet, and the second component is preferably captured within the second chamber between a second piston and a second outlet.

In an embodiment the dispensing tip comprises a cup-shaped socket. The dispensing tip further preferably comprises a cannula that extends through or into the socket. The first seal is preferably provided between the cannula and the outlet (or between the cannula and the first and second outlet). Further, the second seal is preferably provided between the socket and the protective shaft. The dispensing tip preferably has a rear end formed by an end of the socket, and a front end formed by an end of the cannula. The front end of the dispensing tip preferably corresponds to a dispensing end of the cannula. The dispensing end of the cannula is preferably that end at which the substance exists the syringe. Further, the cannula has a connecting end for connecting to the outlet (or to the first and second outlet).

In an embodiment the dispensing tip, in particular the cannula, comprises a static mixer. In use with a syringe storing the substance in the form of a first and second component the first and second component can be mixed within the dispensing tip as they are urged through the static mixer.

In an embodiment the protective shaft comprises a front portion extending at a uniform cross-section along a longitudinal axis. In particular, the front portion preferably has an outer surface that extends at a uniform cross-section along the longitudinal axis. For example the front portion or the outer surface of the front portion may extend at a circular cross-section and thus may be cylindrical. Or the front portion or the outer surface of the front portion may extend at a cross-section based on two side by side circles. Thus the front portion may have a shape of a double-barrel structure. Other shapes are possible. For example the front portion or the outer surface of the front portion may extend at an elliptical cross-section, or the cross-section may be based on a square, a rectangle or any other appropriate shape. Accordingly, the chamber preferably extends at a uniform inner cross-section that is based on the outer cross-section of the cartridge along the longitudinal axis.

The front portion of the protective shaft may form a front end of the protective shaft. Further, the protective shaft has a rear portion that is widened with respect to the front portion. The rear portion preferably forms a rear end of the protective shaft opposite of the front end. Accordingly, the protective shaft may be formed of the first and second portion and the first and second portion are preferably arranged in a stepped configuration.

In an embodiment the syringe comprises a fingerplate. In particular the cartridge preferably has a rear end and may form the fingerplate toward its rear end. The outlet (or the first and second outlet) are preferably arranged at a front end of the cartridge. Preferably, the rear portion of the protective shaft accommodates the fingerplate. Thus, the cartridge may be inserted in a direction from the rear end toward the front end of the protective shaft, with the front end of the cartridge leading and the rear end of the cartridge trailing. Preferably the cartridge snugly fits into the first portion of the protective shaft. A snug fit may be characterized by a maximum play between the cartridge and the front portion, when mated, of 0.5 mm.

In an embodiment the protective shaft is shaped for retaining the cartridge of the syringe within the protective shaft against telescopic movement. The term telescopic movement means a movement of the cartridge and the protective shaft, when mated with each other, relative to each other along the longitudinal axis. The protective shaft is preferably shaped for forming a snap connection with the cartridge of the syringe.

Preferably, the rear portion of the protective shaft has a retention structure behind which the fingerplate is snapped. In particular the rear portion preferably has an inner surface from which the retention structure, for example a bulge, protrudes.

In an embodiment the syringe further comprises a plunger. The plunger is preferably connected to the piston. The connection may be monolithic, co-injected or provided by assembly. In case the connection is monolithic the piston and the plunger are preferably injection molded as one piece. In case the connection is co-injected the piston and the plunger may be injection molded onto each other, for example by first molding the plunger and subsequently molding the piston (or pistons) on the plunger. In case the connection is provided by assembly the piston and the plunger may be plugged onto each other.

The plunger is preferably connected to the piston adjacent a front end of the plunger. The plunger further preferably has a thrust plate that forms a rear end of the plunger. The thrust plate can be used for pushing the plunger forward for dispensing the substance from the syringe.

In an embodiment the protective cover further comprises a protective cap that accommodates the thrust plate. Therefore the protective cap preferably covers the thrust plate. The protective cap preferably is cup-shaped having a bottom wall and a circumferential side wall. The protective cap is preferably shaped for retaining on the plunger, in particular for retaining on the thrust plate. The protective cap further is preferably shaped for forming a snap connection with the plunger, in particular with the thrust plate, of the syringe. The protective shaft may comprise a receptacle for retaining the cap at the protective shaft. The receptacle may be in the form of a pin on which the cap can be received, or any other appropriate structure that is capable of retaining the cap.

In an embodiment the syringe assembly further comprises bellows. The bellows preferably connect the protective cap and the protective shaft with each other. Further, the bellows preferably enclose the plunger. The bellows may for example circumferentially surround the longitudinal axis and may circumferentially surround the plunger. Thus the syringe may be entirely encased by the protective cover, although an entire encasing is optional.

In one embodiment the second seal is provided by a sealing ring that is fixed at the protective shaft. The sealing ring may be co-injected with the protective shaft. Therefore the sealing ring may be made of a material that is different, in particular softer, than the material of the protective shaft. Alternatively the sealing ring may be monolithically formed (from the same material) with the protective shaft. In this case the sealing ring may be provided with one or more sealing lips. Each sealing lip preferably tapers toward a free end of the sealing lip. Therefore the sealing lips may provide the sealing ring with a softness that is sufficient to provide a good seal on the syringe and/or on the dispensing tip.

In an embodiment the protective cover, in particular the protective shaft and the protective cap, are made of a plastic material selected from among PP (polypropylene), COC (cyclic olefin polymer), PC (polycarbonate), ASA (acrylonitrile styrene acrylate), ABS (acrylonitrile-butadiene-styrene terpolymer). The protective cover, in particular the protective shaft and the protective cap, preferably each have a wall thickness of at least 0.2 mm. Thus, the protective cover, in particular the protective shaft and the protective cap, are provided with a geometrically determined shape and provided with a temperature stability that is sufficient for a high level disinfection method. Such a high level disinfection method is typically based on an automatic disinfection in which an object to be disinfected is placed in a device and exposed to chemicals and/or to high temperatures. Film type sleeves are typically not suitable for being disinfected by such a high level disinfection method because they typically fold or collapse during disinfection in a device so that not all relevant surfaces may get reliably disinfected. In contrast, the protective cover has a rigidity that is sufficient to prevent folding and collapsing and thus is suitable to undergo the high level disinfection method.

The invention further relates to a method of removing a protective cover from a syringe assembly of the invention. The method comprises the steps of:

grasping the dispensing tip and the protective shaft and removing the dispensing tip from the cartridge;

grasping the protective shaft and the protective cap, and removing the protective cap from the plunger; and allowing the cartridge to slide off the protective shaft while only holding the protective shaft;

The method allows the use of the syringe without directly touching. Therefore the syringe can be kept clean from bacteria and any other undesired material. Further, the protective cover can be disinfected and re-used so that the invention allows to minimize waste.

DETAILED DESCRIPTION OF THE INVENTION

Figure 1:
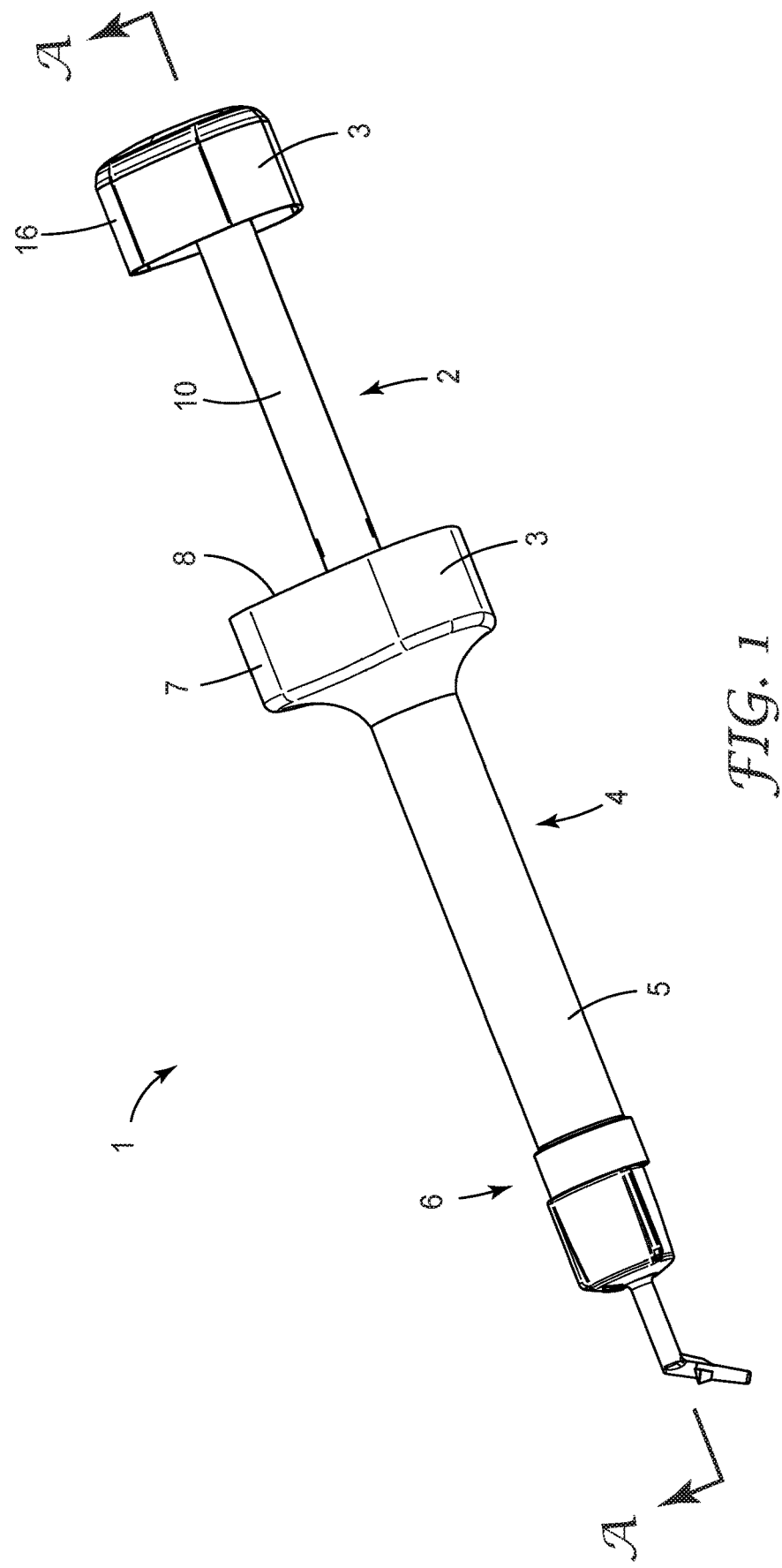
FIG. 1 is a perspective view of a syringe assembly according to an embodiment of the invention.

FIG. 1 shows a syringe assembly 1 according to the invention. The syringe assembly 1 generally comprises a syringe 2 and a protective cover 3.

The syringe 2 is configured for dispensing a dental or medical substance. In particular, the syringe 2 contains a dental or medical substance. In the example the syringe 2 contains a dental substance, for example a dental filling or dental retraction substance.

The protective cover 3 generally comprises or consists of a tubular protective shaft 4 and a cap 16. The protective shaft 4 has a front portion 5. The front portion 5 extends at a uniform cross-section, in the example at a circular cross-section, along a longitudinal axis A. The front portion 5 further forms a front end 6 of the protective shaft 4. The protective shaft 4 further has a rear portion 7 that is widened with respect to the front portion 5. The rear portion 7 forms a rear end 8 opposite of the front end 6 of the protective shaft 4.

Figure 2:
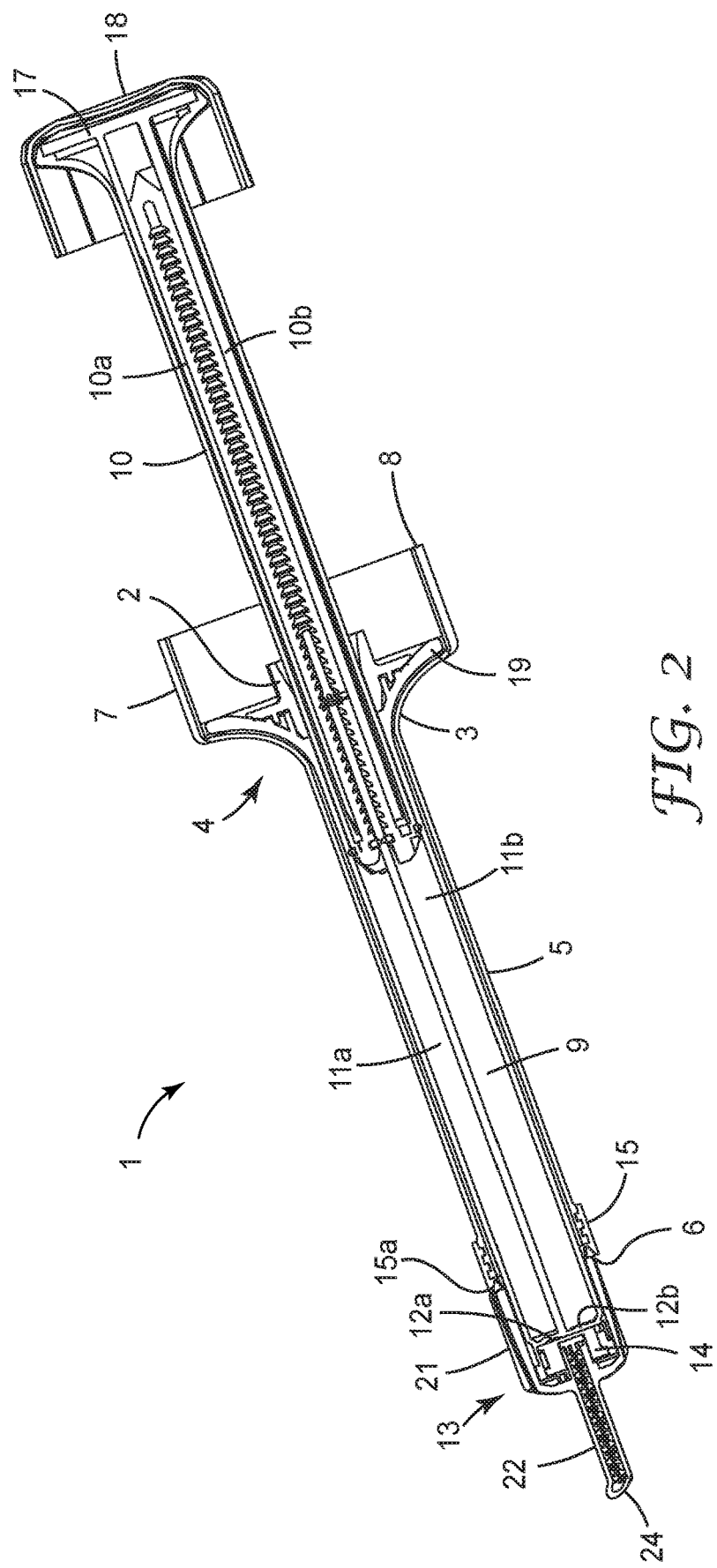
FIG. 2 is a perspective cross-sectional view of a syringe assembly according to an embodiment of the invention.

FIG. 2 shows the syringe assembly 1 of FIG. 1 in a cross-sectional view. The syringe 2 and the protective cover 3 are assembled with each other. In particular, the syringe 2 has a cartridge 9 that is received within the protective shaft 4, in particular within the front portion 5 of the protective shaft 4. In the example the cartridge 9 is configured for holding the substance in the form of two separate components. In particular, the cartridge 9 has a first chamber 11a, and a second chamber 11b for holding the substance in the form of a first and a second component. It is noted that the invention may in another example may have a cartridge having one chamber for holding the substance in the form of a single component. Further, in the example the cartridge 9 has a first and a second outlet 12a, 12b for the substance. The first chamber 11a has the outlet 12a and the second chamber 11b has the outlet 12b. It is noted that the invention may in another example have a cartridge having one chamber for holding the substance in the form of a single component and one outlet for the sub stance.

The syringe 2, in particular the cartridge 9 further comprises a fingerplate 19 which is accommodated, in particular snapped in the rear portion 7 of the protective shaft 4. Therefore a user that operates the syringe assembly 1 does not touch the fingerplate 19 plate directly, but just the protective cover 3. Therefore any undesired material at the user's finger is prevented from reaching the cartridge 9.

The syringe 2 further comprises a dispensing tip 13 that in the example is connected to the first and second outlet 12a, 12b. The dispensing tip 13 is configured for mixing the first and second component with each other and for dispensing the substance from the dispensing tip 13.

Figure 3:
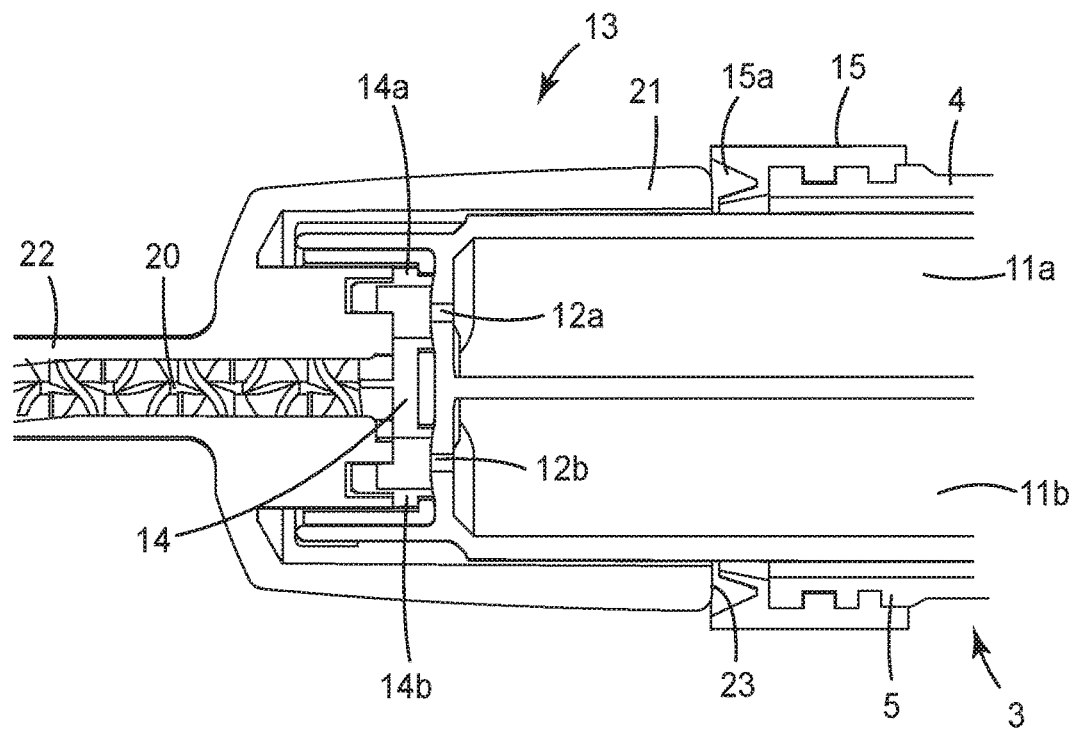
FIG. 3 is a detail view of the syringe assembly shown in FIG. 2.
Figure 4:
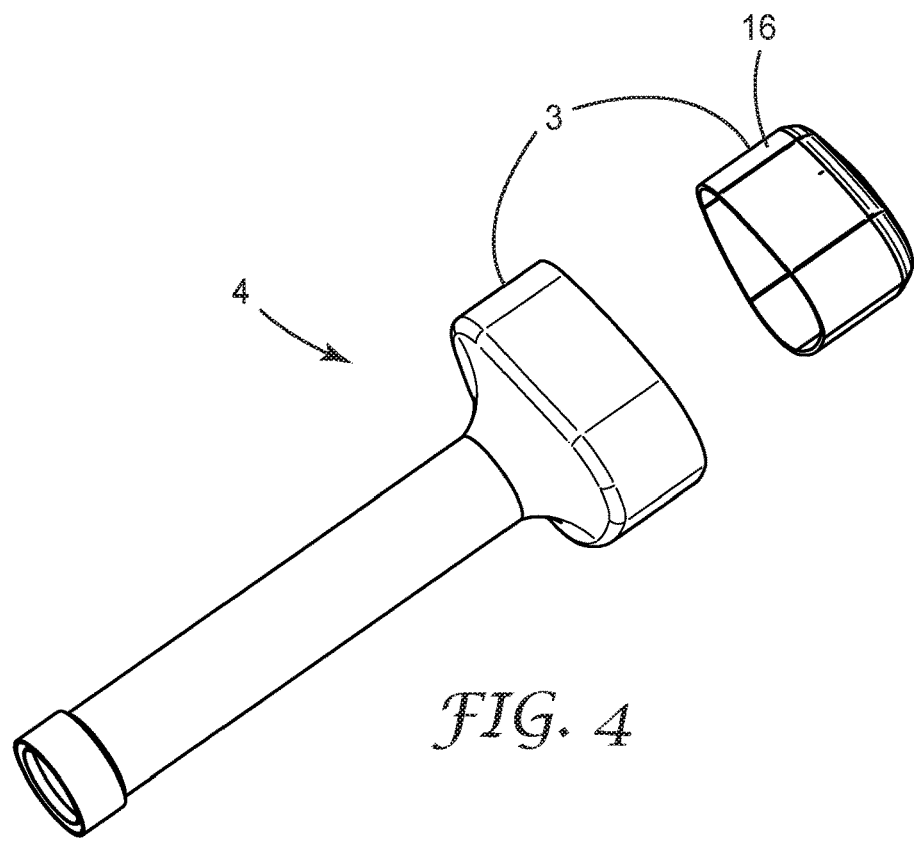
FIG. 4 is a perspective view of a protective cover as it may be used in an embodiment of the invention.

As shown in FIG. 3 between the dispensing tip 13, on the one hand, and the first and second outlet 12a, 12b, on the other hand, a first seal 14 is provided. In the example the first seal 14 is provided by a first gasket 14a and a second gasket 14b. In the example the first and second gasket 14a, 14b are provided by a static mixing element 20 that is received within the dispensing tip 13.

A second seal 15 is provided between the dispensing tip 13 and the protective cover 3, in particular between the dispensing tip 13 and the protective shaft 4. In the example the second seal 15 is provided in the form of a sealing ring that surrounds the front portion 5 of the protective shaft 4. The second seal 15 further has a pair or circumferential sealing lips 15a which engage a rear end 23 of the dispensing tip 13.

The dispensing tip has a cup-shaped socket 21 and a cannula 22. The cannula 22 extends into the socket 21. The first seal 14 is provided within the socket 21, between the cannula 22 and the first and second outlet 12a, 12b. Further, the second seal 15 is provided between the socket 21 and the protective shaft 4. The rear end 23 of the dispensing tip 13 is preferably formed by an end of the socket 21. A front end 24 (see FIG. 2) of the dispensing tip 13 is formed by an end of the cannula 22. The front end 24 further forms a front end of the syringe assembly 1.

As shown in FIG. 2 in the syringe 2 has a plunger 10 for expelling the substance from the syringe 2. In the example the plunger 10 has a first plunger element 10a and a second plunger element 10b for cooperation with the first and second chamber 11a, 11b, respectively. In particular, a front end of each of the first and second plunger element 10a, 10b are received within the first and second chamber 11a, 11b, respectively. Further, the plunger 10 has a thrust plate 17 that forms a rear end 18 of the plunger 10. The cap 16 covers the thrust plate 17. Therefore a user that operates the syringe assembly 1 does not touch the thrust plate directly, but just the protective cover 3. Therefore any undesired material at the user's finger is prevented from reaching the plunger 10.

Figure 5:
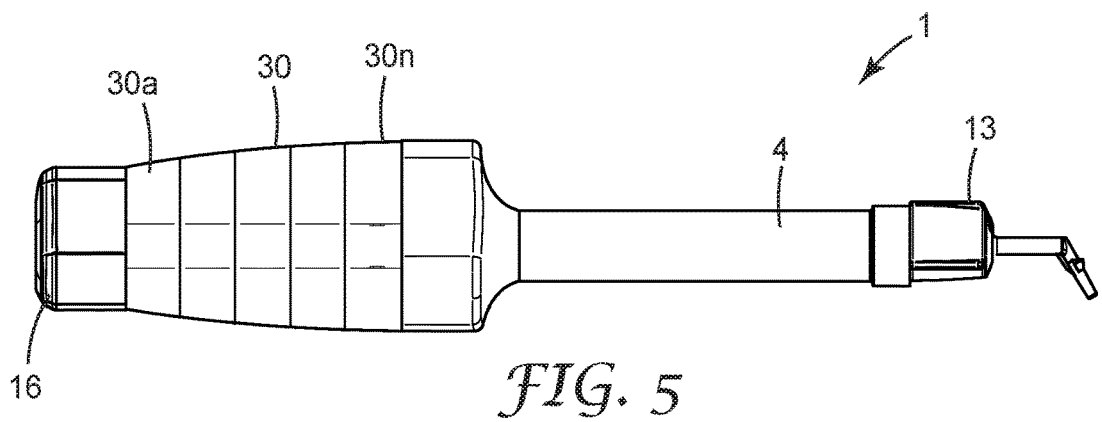
FIGS. 5-10 are side views of syringe assemblies according to embodiments of the invention.
Figure 6:
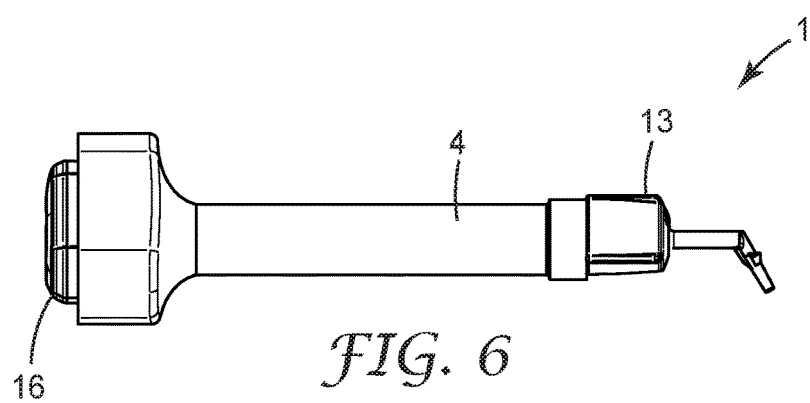

FIGS. 5 to 10 each show the syringe assembly 1 according to the invention in combination with various embodiments of a bellow 30/31/32. FIGS. 5 and 6 show bellows 30 that comprise a plurality of telescopically engaging rings 30a to 30n. The number of rings 30a-30n can be determined as desired and depends, inter alia, on a distance between the protective cap 16 and the protective shaft 4 that is to be bridged by the bellows 30. The number of rings 30a-30n further depends on a length of each ring 30a-30n. FIG. 5 shows the syringe assembly 1 at a retracted stage, whereas FIG. 6 shows the syringe assembly 1 at a fully emptied stage. At the retracted stage the bellows 30 cover the plunger 10. Therefore in combination of the bellow 30, the dispensing tip 13, the protective shaft 4 and the cap 16 the syringe 2 is entirely encased. At the fully emptied stage the rings 30a to 30n are fully arranged within each other.

Figure 7:
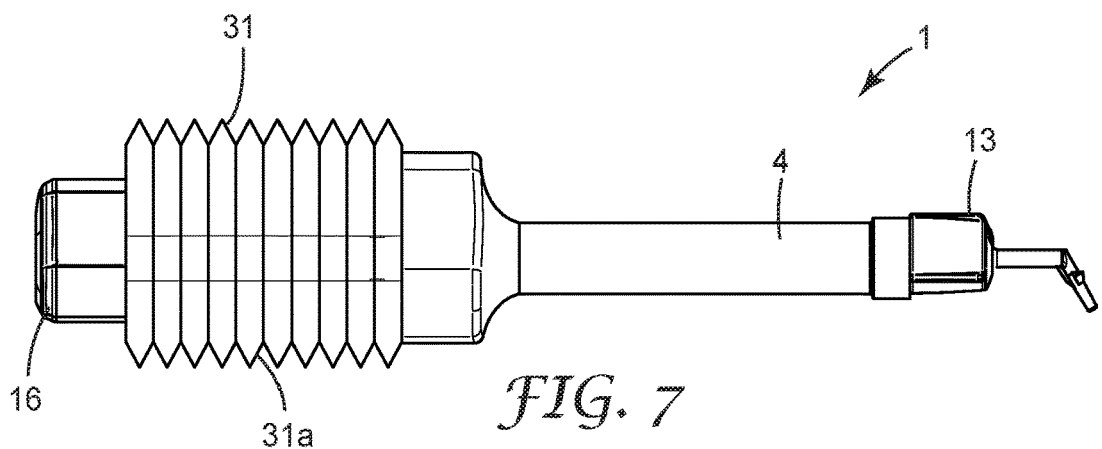
Figure 8:
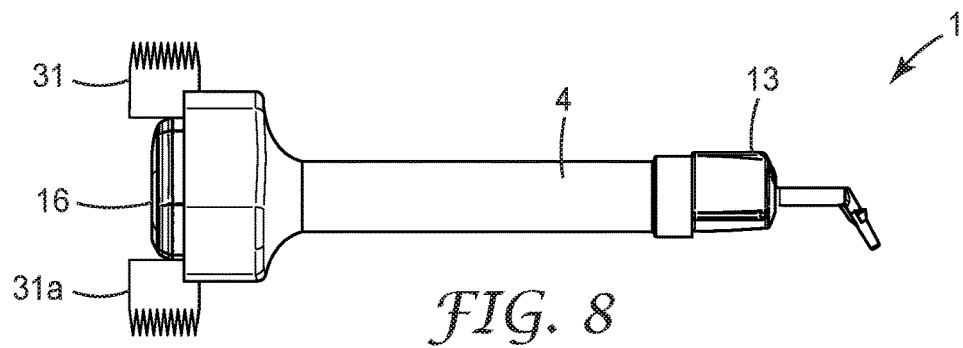

FIGS. 7 and 8 show bellows 31 that is has a collapsible wall 31a. The collapsible wall 31a is pre-formed based on a zigzag-shape that provides for a pre-determined collapsing. FIG. 7 shows the syringe assembly 1 at a retracted stage, whereas FIG. 8 shows the syringe assembly 1 at a fully emptied stage. Again, at the retracted stage the bellows 31 cover the plunger 10. Therefore in combination of the bellows 31, the dispensing tip 13, the protective shaft 4 and the cap 16 the syringe 2 is entirely encased.

Figure 9:
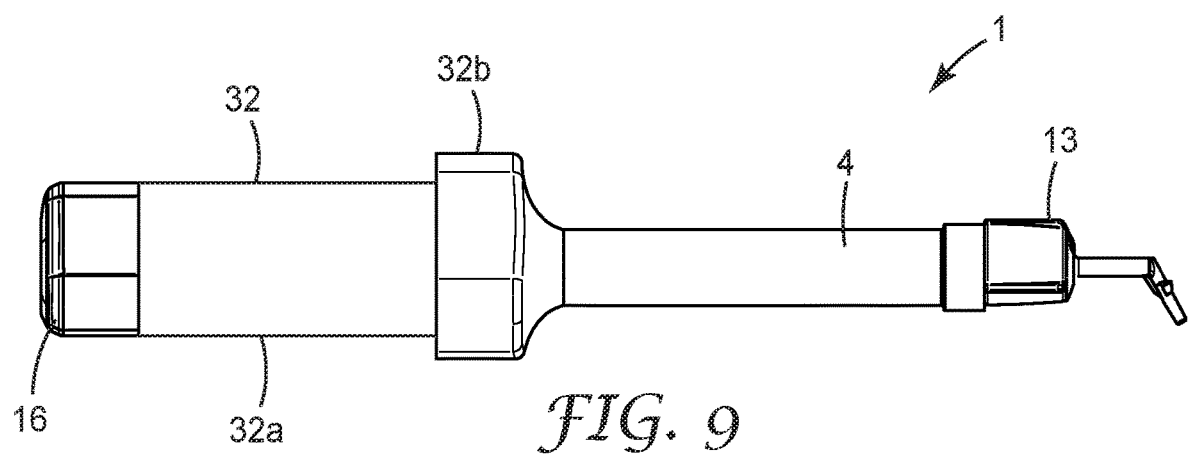
Figure 10:
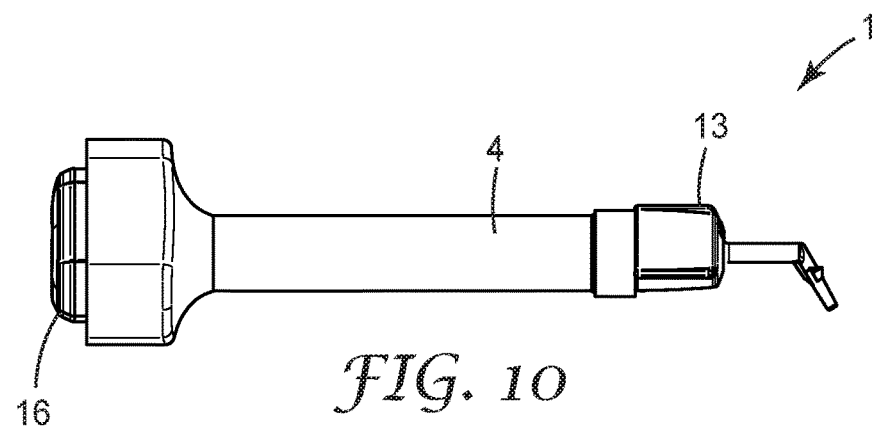

FIGS. 9 and 10 show bellows 32 that is has a retractable wall 32a. The retractable wall 32a is made of a foldable film. The syringe assembly 1 has a wind-up-roller 32b that winds up the retractable wall 32a upon use of the syringe assembly 1 for dispensing.

FIG. 9 shows the syringe assembly 1 at a retracted stage, whereas FIG. 10 shows the syringe assembly 1 at a fully emptied stage. As before, at the retracted stage the bellows 32 cover the plunger 10. Therefore in combination of the bellows 32, the dispensing tip 13, the protective shaft 4 and the cap 16 the syringe 2 is entirely encased.

What is claimed is:

1. A syringe assembly, comprising a syringe for dispensing a dental or medical substance, and a protective cover configured for encasing at least a portion of the syringe that comprises a tubular protective shaft, wherein the syringe is configured so that it can be operated with or without the protective cover, wherein the syringe has a cartridge, and wherein the cartridge and the protective cover are assembled with the cartridge being received within the protective shaft, wherein the cartridge comprises an outlet for the substance, wherein the syringe further comprises a dispensing tip that is connected to the outlet for dispensing the substance from the dispensing tip, and wherein a first seal is provided between the dispensing tip and the outlet, and a second seal is provided between the dispensing tip and the protective shaft.

2. The syringe assembly of claim 1, wherein the cartridge forms a chamber for the substance, wherein the syringe assembly further comprises a piston received within the chamber for expelling the substance from the chamber.

3. The syringe assembly of claim 1, wherein the dispensing tip comprises a cup-shaped socket, wherein the second seal is provided between the socket and the protective shaft.

4. The syringe assembly of claim 3, wherein the dispensing tip further comprises a cannula that extends through the socket, wherein the first seal is provided between the cannula and the outlet.

5. The syringe assembly of claim 1, wherein the protective shaft comprises a front portion extending at a uniform cross-section along a longitudinal axis, the front portion forming a front end of the protective shaft, and wherein the protective shaft further has a rear portion that is widened with respect to the front portion, the rear portion forming a rear end of the protective shaft opposite of the front end.

6. The syringe assembly of claim 5, wherein the syringe comprises a fingerplate and wherein the rear portion of the protective shaft accommodates the fingerplate such that a user cannot touch the fingerplate directly.

7. The syringe assembly of claim 6, wherein the protective shaft is shaped for retaining the cartridge of the syringe within the protective shaft against telescopic movement, wherein in particular the rear portion of the protective shaft having a retention structure behind which the fingerplate is snapped.

8. The syringe assembly of claim 2, wherein the syringe further comprises a plunger being connected to the piston adjacent a front end of the plunger and having a thrust plate forming a rear end of the plunger, and wherein the protective cover further comprises a protective cap that accommodates the thrust plate.

9. The syringe assembly of claim 8, further comprising bellows connecting the protective cap and the protective shaft with each other and enclosing/surrounding the plunger.

10. The syringe assembly of claim 1, wherein the protective cover is removably attached to the syringe.

11. The syringe assembly of claim 1, wherein the protective shaft is made of a plastic material selected from among PP (polypropylene), COC (cyclic olefin polymer), PC (polycarbonate), ASA (acrylonitrile styrene acrylate), ABS (acrylonitrile-butadiene-styrene terpolymer).

12. A method of removing a protective cover from a syringe assembly of claim 1, the method comprises the steps of:
    grasping the dispensing tip and the protective shaft and removing the dispensing tip from the cartridge;
    grasping the protective shaft and the protective cap, and removing the protective cap from the plunger; and
    allowing the cartridge to slide off the protective shaft while only holding the protective shaft.

* * * * *